United States Patent [19]

Thomas

[11] Patent Number: 4,513,866
[45] Date of Patent: Apr. 30, 1985

[54] EMERGENCY MEDICAL PACK

[76] Inventor: Frank O. Thomas, 5167 South 600 East, Murray, Utah 84107

[21] Appl. No.: 428,103

[22] Filed: Sep. 29, 1982

[51] Int. Cl.³ .............................................. A45C 11/00
[52] U.S. Cl. .................................. 206/570; 190/110; 190/111; 206/373; 206/803
[58] Field of Search ................ 150/7, 52 J, 52 R; 190/41 B, 41 C, 41 R, 41 Z, 42, 43, 49, 52, 53, 59, 60, 61, 102, 106, 109–111, 122; 206/372, 373, 376, 570, 803, 459; 224/151, 153, 209, 215

[56] References Cited

U.S. PATENT DOCUMENTS

| D. 230,327 | 2/1974 | Cooperstein . | |
|---|---|---|---|
| D. 231,868 | 6/1974 | Ohyama . | |
| 1,653,246 | 12/1927 | Zichy | 190/51 |
| 1,705,149 | 3/1929 | Brady . | |
| 2,324,194 | 7/1943 | Campiglia . | |
| 3,019,952 | 2/1962 | Brewster . | |
| 3,622,056 | 11/1971 | Droeger . | |
| 3,759,356 | 9/1973 | Bostick et al. | 190/52 |
| 3,926,234 | 12/1975 | Dean | 206/459 |
| 4,169,550 | 10/1979 | Williams . | |
| 4,236,657 | 12/1980 | Brunton . | |
| 4,241,833 | 12/1980 | Luebcke | 190/52 |
| 4,342,390 | 8/1982 | Mitchell et al. | 206/372 |
| 4,386,642 | 6/1983 | Durbin | 206/570 |

Primary Examiner—George E. Lowrance
Assistant Examiner—Jimmy G. Foster
Attorney, Agent, or Firm—Workman, Nydegger & Jensen

[57] ABSTRACT

An emergency medical pack for storing and transporting emergency medical equipment is provided with a lid which has operable positions of at least a closed position, a half-open position and a fully opened position. Pockets are provided in the pack to hold the medical equipment and are arranged such that all of the equipment can be accessed in confined spaces when the pack is in the half-open position as well as when it is in the fully open position. Unique open drawer pockets are located within the pack and are accessible either through the open ends or by opening the top flaps.

25 Claims, 14 Drawing Figures

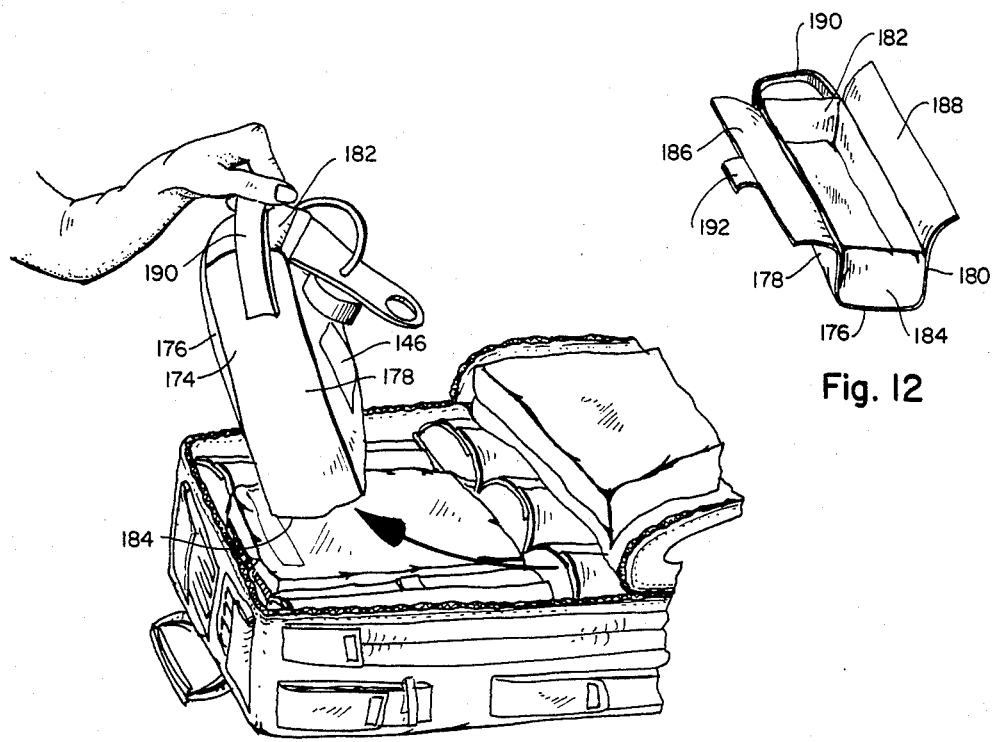
Fig. 11
Fig. 12
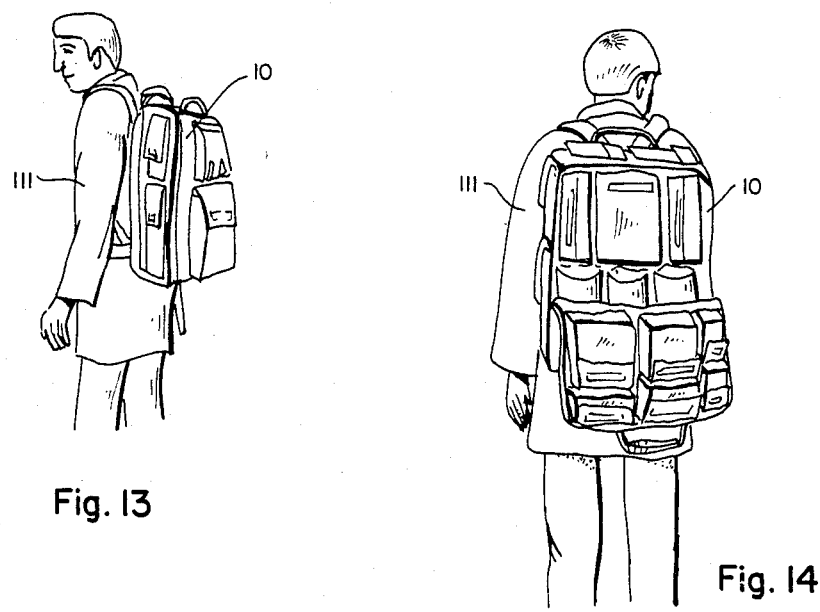
Fig. 13
Fig. 14

EMERGENCY MEDICAL PACK

BACKGROUND

1. The Field of the Invention

The present invention relates to readily transportable apparatus used in handling and storing numerous, independent equipment components, and more particularly, this invention is directed to a portable pack for storage of emergency medical equipment wherein all of the stored components are readily and independently accessible, even in confined areas.

2. The Prior Art

For the critically ill or severely injured victim, the difference between life and death often depends upon the immediate institution of life saving measures and treatment at a remote location before transporting the victim to a hospital. The institution of these life saving measures in an attempt to stabilize the victim prior to transportation requires the use by medically trained personnel of various components of specialized equipment.

For the patient who becomes seriously ill or injured away from the setting of the hospital, life saving treatment necessitates that this equipment and the specially trained personnel arrive rapidly at the scene. In recent years, the use of paramedics and other specially trained personnel to treat the seriously ill or injured at remote locations has increased dramatically. Indeed, even the use of helicopters and airplanes to transport such personnel and their equipment to the victim has become standard in many localities.

One of the major problems which has been encountered with the increased use of emergency vehicles is the confined space restrictions. Because the amount of space in an emergency vehicle is very limited, limitations are necessarily placed on the types and amounts of emergency medical equipment which can be transported. In an attempt to transport as much equipment as possible, the result is the critical need to organize and store the medical equipment in such a manner that it can be used in the emergency vehicle and still be hand-carried to the location of the victim.

An emergency medical pack capable of carrying the necessary life saving equipment to the location of the patient must be portable, lightweight, and easily carried. It must also allow easy identification of equipment and rapid entry into the equipment containing compartments while providing needed protection for the specialized equipment in order to avoid damage or loss.

One of the major problems with presently designed emergency medical packs is the inability to rapidly access needed emergency medical equipment both at the scene and in areas of confinement, i.e., ambulances, airplanes, and helicopters. Presently designed packs capable of carrying the specialized equipment are typically not suited for use in such confined spaces. Frequently, such packs permit access to their contents only through a single opening in one portion of the pack or by fully opening panel members in the manner of conventional suitcases. In the use of packs having only a single opening for access, it will be readily appreciated that rapid identification and recovery of desired items from deep within the pack can be extremely difficult. Although the panel opening packs used in the prior art somewhat reduce this problem, the additional room required for their use has generally made it impractical, if not impossible, to use them in the confined spaces within ambulances, helicopters, airplanes, and the like. Additionally, some victims such as injured hikers are often located in crevices or on ledges, and the use of prior art packs even at the location of the patient can be severely restricted.

The inability to readily access needed specialized equipment in confined areas delays the implementation of life saving treatment required in major medical emergencies. Such delays may indeed make the difference between life or death, and certainly these delays can increase the likelihood and extent of resultant permanent injury. It is, therefore, of utmost importance that all equipment be readily accessible during the transport of patients in these areas of confinement.

Another problem that is often encountered while treating accident victims at the scene is the inability to effectively treat more than one person at a time. Although more than one medically trained person may be at the scene, it is seldom the case that two or more full sets of equipment are there. There is usually only one pack containing all of the equipment and that pack has to be transferred from victim to victim. No provisions have been made in prior art packs to arrange the equipment so that parts of it can be safely and effectively removed and utilized on another victim while the pack remains near the first victim or in a central location.

Accordingly, it would be a significant advancement in the art to provide an emergency medical pack which could carry most of the necessary medical equipment to reach and treat seriously ill or injured persons both at remote locations accessible only by foot, as well as during the time they are being transported to a hospital by ambulance, helicopter, or airplane. It would be a further advancement in the art to provide an emergency medical pack wherein all of the equipment contained therein is readily accessible and identifiable, even in confined areas. It would also be an advancement in the art to provide an emergency medical pack wherein various pieces of equipment could be removed in separate pouches such that it could be safely transported to treat other accident victims. Such apparatus are described and claimed herein.

BRIEF SUMMARY AND OBJECTS OF THE INVENTION

The present invention relates to a novel emergency medical pack used to transport equipment necessary to provide advanced medical care to a critically ill or injured patient. The pack includes a number of pockets which hold, protect, and allow rapid access to needed emergency medical equipment. The pack is configured to be easily transported by a person traveling on foot, and to provide for rapid access to its contents during use in confined spaces, such as while transporting the patient in the confined area of an ambulance, helicopter or airplane.

The pack has a generally rectangular box shape with the front portion forming a lid which is preferably zippered on three sides to provide ready access to the interior contents. The lid is designed such that it can be positioned in a closed position, a half-open position, or a fully opened position. The pack can either be carried by hand utilizing handles located on the top of the pack or it can be worn as a backpack if it must be carried for greater distances or if the bearer needs to have both hands free.

The design of the pack is such that the lid can be unzipped halfway and folded back on itself in a "half-open" configuration while still permitting ready access to all of the contents of the bag. Of particular significance is the fact that all of the contents of the pack can be readily accessed when the lid is in the half-open position, as well as when it is in the fully open position. This is significant because it is often difficult or impossible to fully open the prior art packs so as to access all of their contents while in areas of confinement such as ambulances, helicopters or airplanes.

Pockets are located in the body of the pack as well as in the lid and on the sides of the pack to hold and protect the medical equipment. Specially designed pockets referred to as "open drawer pockets" are located in the bottom portion of the body of the pack. These pockets can either be accessed through an open end located at about the midline of the pack, if the pack is in the half-open or full-opened position, or they can be accessed from above by opening the pocket along its length if the pack is in the fully opened position. Located within these open drawer pockets are separate pouches containing the medical equipment. These pouches facilitate removal of equipment from the pack and also allow the equipment to be carried to another patient without having to move the entire pack.

It is, therefore, a primary object of this invention to provide an emergency medical pack wherein all of the contents can be readily identified and accessed even in confined areas.

It is a further object of this invention to provide an emergency medical pack which provides protection, storage, and rapid accessibility of life saving equipment, and which can be easily transported to the seriously ill or injured person.

It is still a further object of the invention to provide a pack wherein the contents can be divided and safely dispersed to treat more than one patient at a time.

These and other objects and features of the present invention will become more fully apparent from the following description and appended claims taken in conjunction with the accompanying drawings.

BRIEF DESCRIPTION OF THE DRAWINGS

FIG. 11 is a perspective view of a portion of the emergency medical pack in a half-open position illustrating a piece of equipment in an internal pouch after it has been removed from one of the open drawer pockets.

FIG. 12 is a perspective view of an equipment carrying pouch to illustrate its configuration.

FIG. 13 is a perspective view of a person wearing the emergency medical pack on his back in the closed position.

FIG. 14 is a perspective view of a person wearing the emergency medical pack on his back in the half-open position wherein an associate can have access to all of the contents of the pack.

DETAILED DESCRIPTION OF THE PREFERRED EMBODIMENTS

The present invention is best understood by reference to FIGS. 1-11 wherein like numerals designate like parts throughout.

Figure 1:
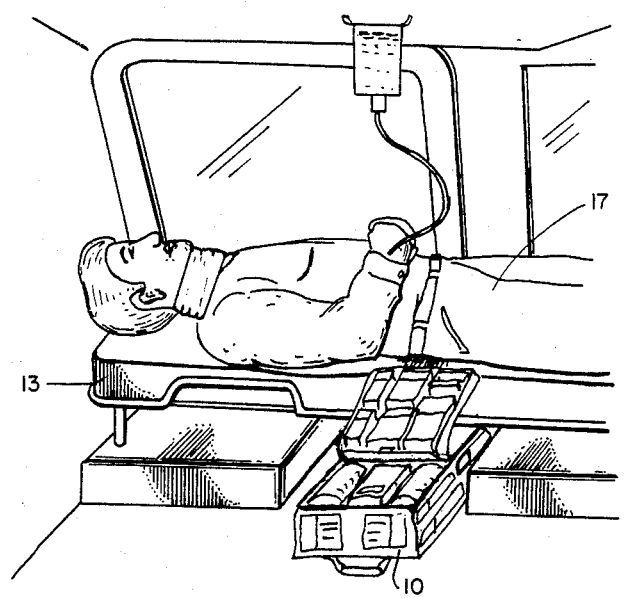
FIG. 1 is a perspective view of the cargo compartment of an ambulance or helicopter showing a patient on a stretcher with an emergency medical pack within the scope of the present invention stored in the half-open position in the space below the stretcher.

FIG. 1 illustrates emergency medical pack 10 being stored in the half-open position below the stretcher 13 on which a victim 17 is lying in an emergency vehicle. Generally, there is very limited space within emergency vehicles and the ability to have access to all of the medical equipment while pack 10 is only in the half-open position could mean the difference between life and death for a victim.

Figure 2:
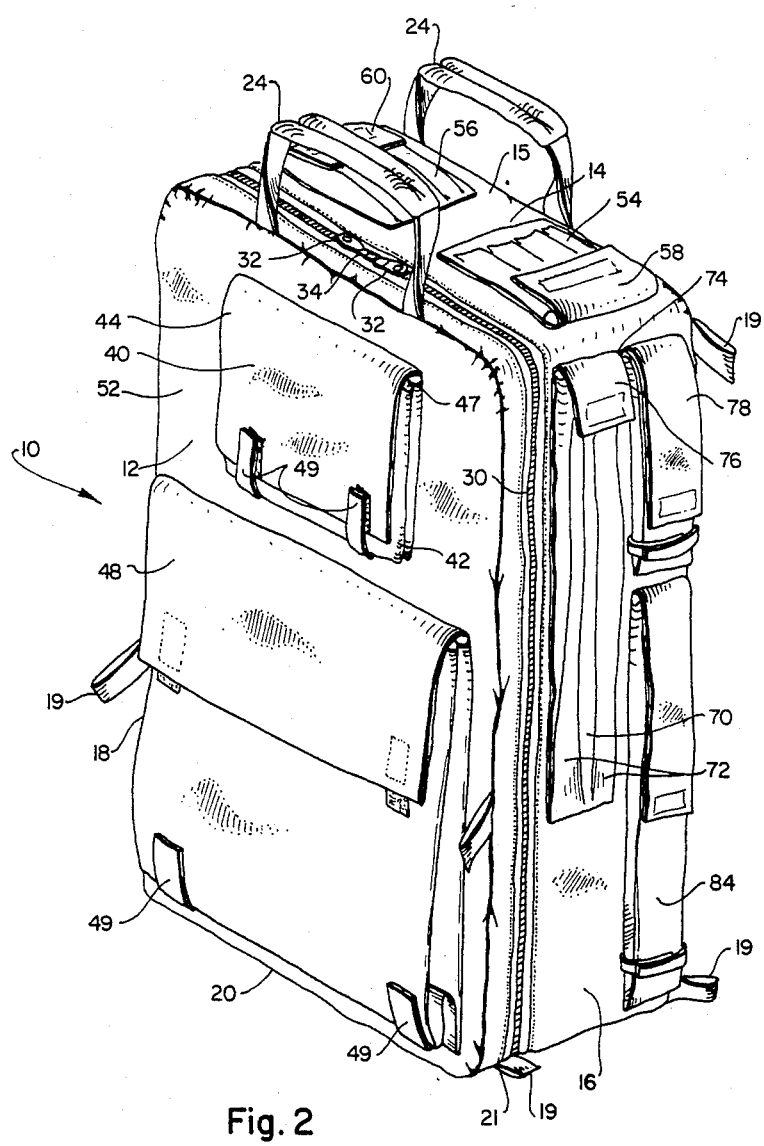
FIG. 2 is a front perspective view of an emergency medical pack of the present invention as it is standing upright in the closed position.
Figures 4, 5:
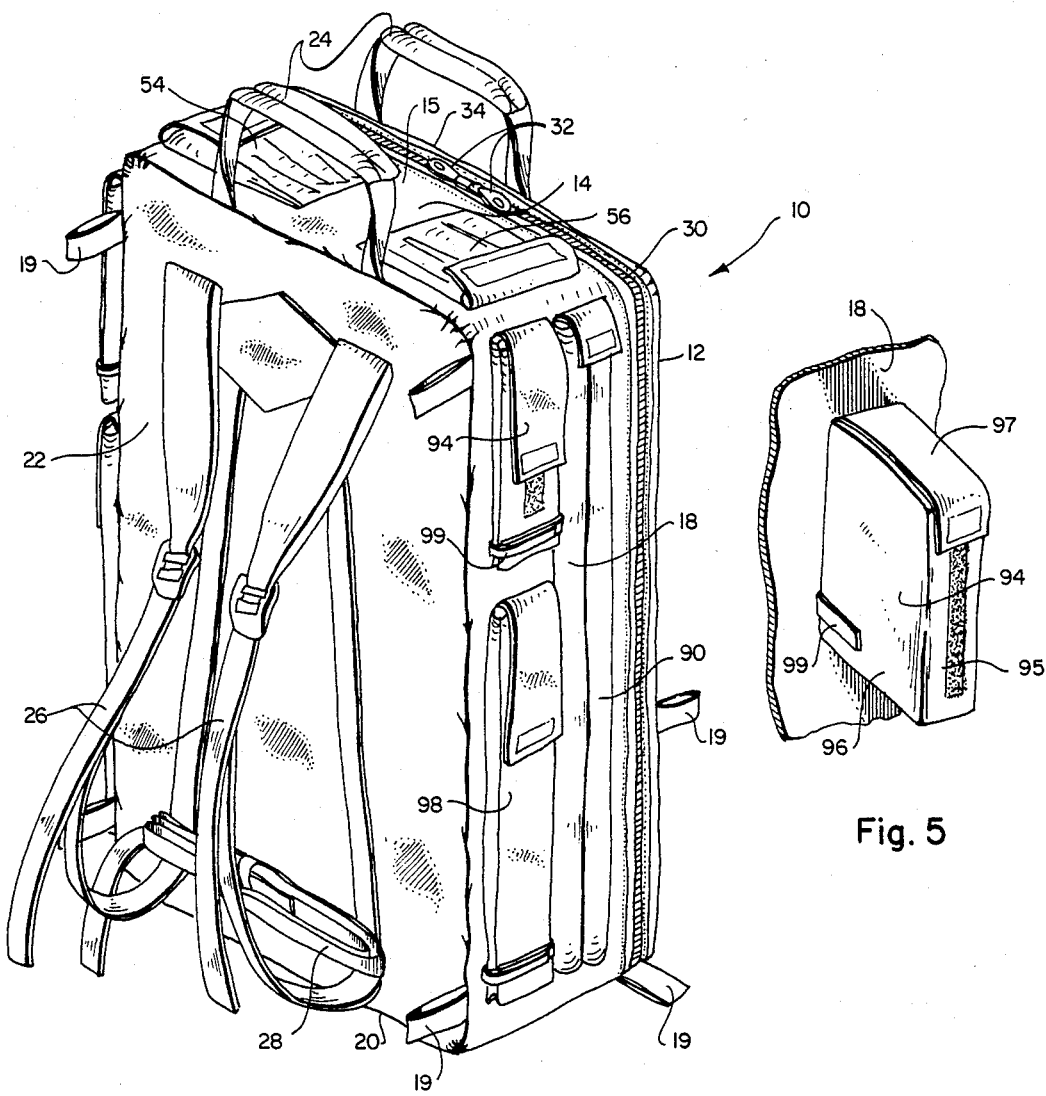
FIG. 4 is a rear perspective view of an emergency medical pack of the present invention as it is standing upright in the closed position.
FIG. 5 is a perspective view of another external pocket in its expanded position, which pocket is attached to an emergency medical pack.

The emergency medical pack 10 of the present invention is illustrated from the front and rear in the closed position in FIGS. 2 and 4. The front 12 of the emergency medical pack 10, is illustrated in FIG. 2, is generally rectangular in shape. Pack 10 further comprises a top 14, right side 16, left side 18, bottom 20, and back 22. Handles 24 are attached to the front 12 adjacent top 14 and the back 22 adjacent top 14. Handles 24 allow pack 10 to be hand carried for short distances.

Shoulder straps 26 and belt strap 28 (see FIG. 4) are attached to back 22 of pack 10 so that pack 10 may be worn as a backpack. This is important if pack 10 must be carried a great distance or if the carrier needs both hands free while carrying the pack to provide medical services. Also included on pack 10 are stabilizing loops 19. Loops 19 are included so that pack 10 can be tied down to prevent it from sliding around during rough rides.

Figures 7, 8:
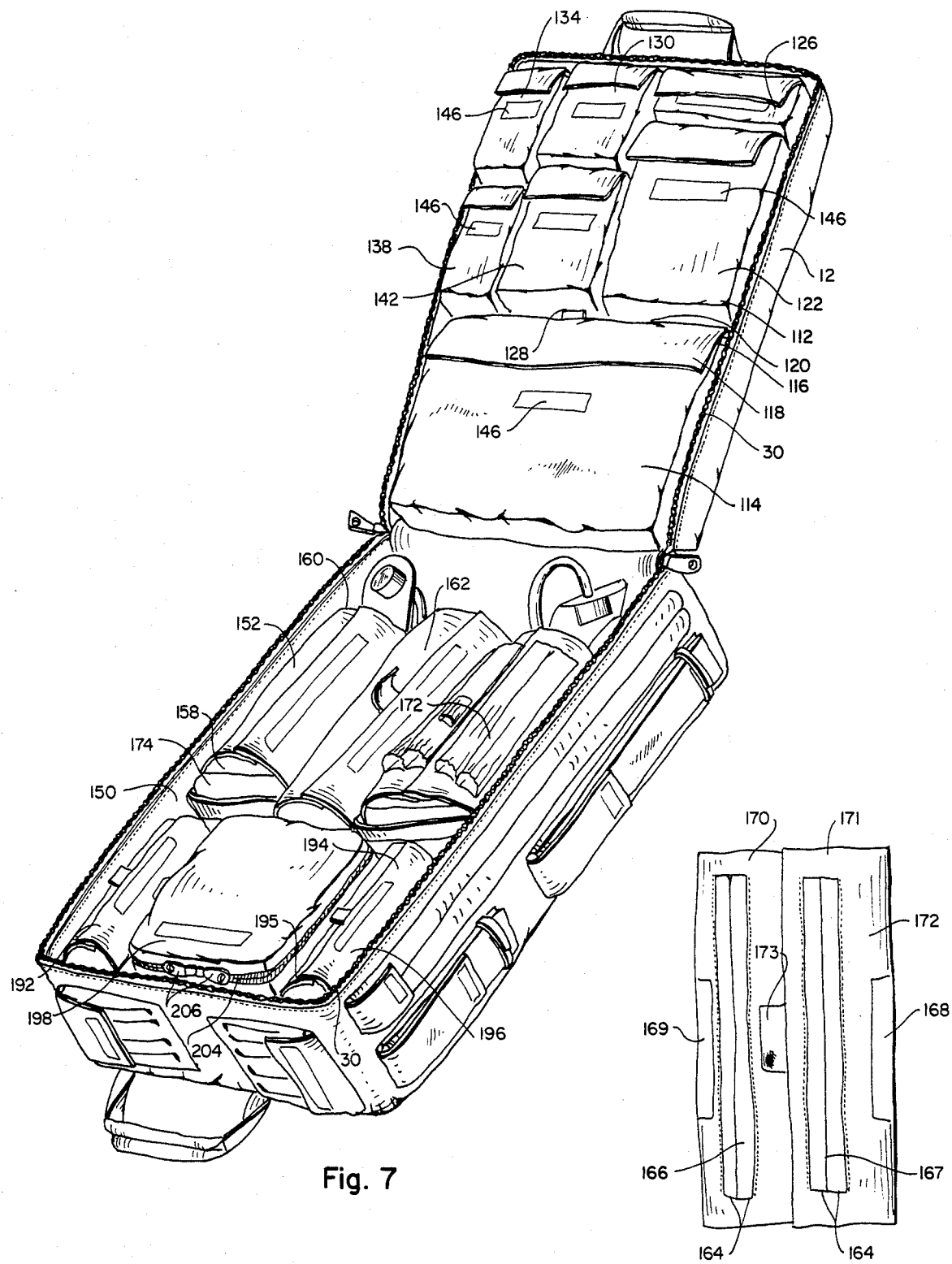
FIG. 7 is a perspective view of an emergency medical pack, of the present invention in the fully opened position illustrating interior pockets of the pack.
FIG. 8 is a top view of a open drawer pocket of the present invention illustrating the small additional pockets which are located on the top and sides thereof.

Front 12 is hingedly connected to bottom 20 along edge 21 (see also FIG. 7). A zipper 30 extends along the remaining three sides of front 12 and along sides 16 and 18 and top 14 of pack 10. Zipper 30 sealingly attaches front 12 to top 14 and sides 16 and 18 when pack 10 is in the closed position.

In the preferred embodiment, zipper 30 is one continuous piece and has two slides 32 for opening and closing the zipper. When pack 10 is in the closed position, slides 32 meet at approximately the center 34 of top 14. Alternatively, zipper 30 could be comprised of two separate zippers, one on each side of the pack, extending from center 34 to the bottom of the respective sides. Additionally, it will be recognized by those skilled in the art that other means could be used to close the pack.

Pack 10 is equipped with numerous internal and external pockets to hold specialized medical apparatus which are stored within the pack. Illustrated in FIG. 2 are exterior pockets 40 and 48 which are located on exterior surface 52 of front 12. Pocket 40 comprises a body 42 which is attached along three edges thereof to front 12, and flap 44. Flap 44 is attached along one edge to front 12 and is secured over the opening 47 in the top of pocket 40 by fasteners 46 (see FIG. 3) which anchor it to body 42. In the preferred embodiment, fasteners 46 comprise strips of fabric onto which hook and loop fasteners (commonly referred to by the trademark Velcro) are attached. Pocket 40 is shown in FIG. 2 in the collapsed position.

Figure 3:
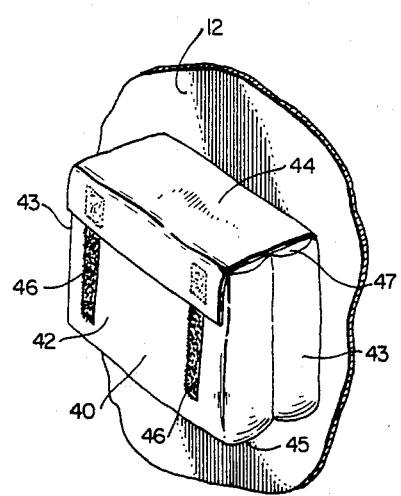
FIG. 3 is a perspective view of an external pocket in its expanded position, which pocket is attached to an emergency medical pack of the present invention.

FIG. 3 illustrates pocket 40 in the expanded position. Sides 43 and bottom 45 of pocket 40 are pleated such that pocket 40 can expand to hold equipment of different sizes. Fasteners 46 and 49 (see FIG. 2) are attached to the top and bottom of pocket 40 respectively to prevent the top and bottom from extending outwardly when only small or thin equipment is stored within pocket 40. Fasteners 49 are straps of material fastened at one end to front 12 and are looped over the bottom of pocket 40 and are secured with Velcro attached to the other end.

Returning again to FIG. 2 pocket 48 is located below pocket 40 on front 12 and is similar in construction to pocket 40 except that it is larger.

Slotted pockets 54 and 56 are shown located on the exterior surface 15 of top 14. Pockets 54 and 56 are attached to top 14 by a suitable means such as by sewing. In the illustrated embodiment, pocket 54 is divided into four longitudinal slots running the length thereof and pocket 56 is divided into three longitudinal slots. These slots are designed to hold syringes or other similarly shaped equipment. Flaps 58 and 60 cover the open ends of pockets 54 and 56, respectively, to prevent the equipment from falling out and are fastened, in the preferred embodiment, by Velcro closures.

As illustrated in FIGS. 2 and 4, the exterior surface of sides 16 and 18 are also equipped with pockets. Side 16 has a slotted pocket 70 running along a substantial length thereof. In the illustrated, preferred embodiment, pocket 70 has two longitudinal slots 72 which are designed to hold catheters or other similar equipment. Openings 74 are located in the top of slots 72 to provide access to the equipment stored therein. Flap 76 covers openings 74 to prevent equipment from falling out and to prevent dirt or other foreign material from entering the pockets. Flap 76 is also secured by Velcro fasteners.

Located adjacent pocket 70 on side 16 are expandable pockets 78 and 84. These pockets are similar in construction to pockets 40 and 48 on front 12 but are considerably narrower. It will be readily appreciated the precise shape and orientation of the pockets with respect to each other may vary depending upon the equipment to be carried and stored.

Side 18, best illustrated in FIG. 4, also includes three exterior pockets. Slotted pocket 90 is similar to slotted pocket 70 on side 16 except that it is longer to accommodate different sized equipment, such as longer catheters. Expandable pockets 94 and 98 are located adjacent slotted pocket 90 and are substantially identical to pockets 78 and 84. Expandable pocket 94 is illustrated in its expanded position in FIG. 5. Pocket 94 includes front 95, sides 96, and top flap 97. Flap 97 is fastened to front 95 by a Velcro closure. Strap fastener 99 is also included to hold the bottom of pocket 94 closed when the pocket is in the collapsed position and is also secured by a Velcro fastener.

Figure 6:
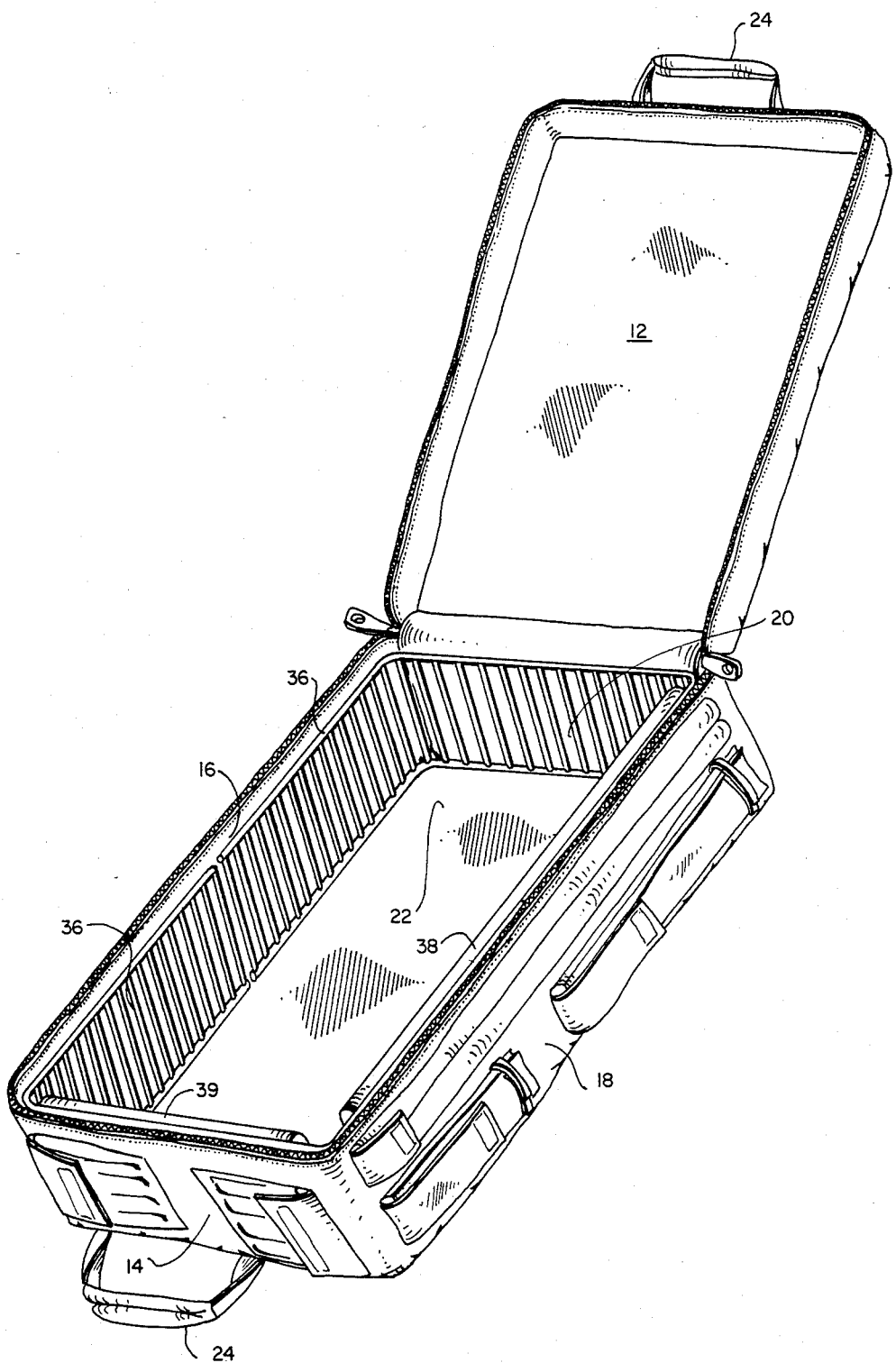
FIG. 6 is a perspective view of an emergency medical pack of the present invention in the fully opened position wherein the pockets and most of the contents have been removed to illustrate the body structure of the emergency medical pack.

FIG. 6 illustrates pack 10 in the full-open position without any of its internal pockets and without most of its contents. Front 12, top 14, sides 16 and 18, bottom 20, and back 22 are preferably made from nylon fabric or other similar material. Ladder splint 36 is positioned along the interior of sides 16 and 18, top 14, and bottom 20 in the preferred embodiment to provide rigidity to the sides of pack 10 when it is not being used. It can easily be removed and utilized if the treatment of a victim necessitates its use. Removable cushioned 38 and 39 arm splints (shown only on two sides of pack 10) are attached to ladder splint 36. These splints can easily be removed and utilized when the need arises. When splints 38 and 39 are not being used to treat a victim, they provide additional support and protection to the medical instruments and equipment which are located within the pack. Back 22 of pack 10 is preferably made from layers of material with a cushion pad (not shown) located therebetween. The use of ladder splint 36, arm splints 38 and 39, and the cushion pad located in the back of the pack provides sufficient rigidity such that additional frame means are not required to support the pack while it is being carried on a persons back.

Figure 9:
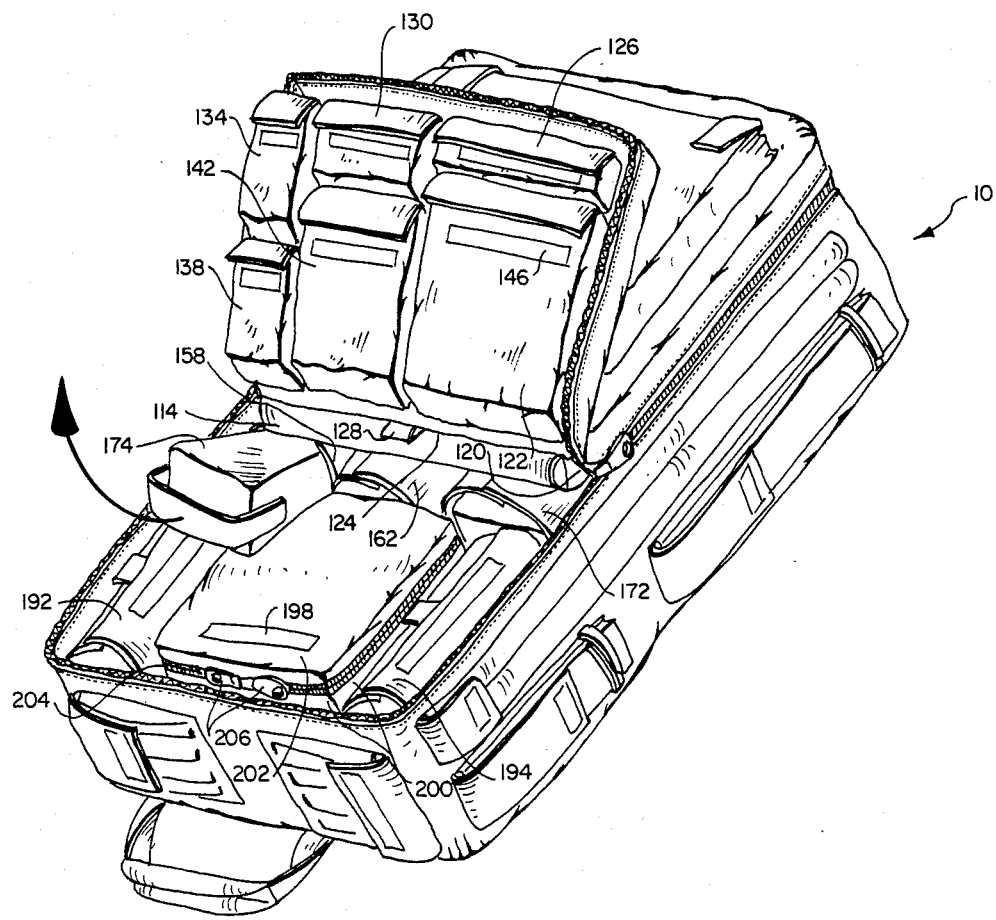
FIG. 9 is a perspective view of an emergency medical pack in the half-open position illustrating the removal of the contents from one of the open drawer pockets.

Pack 10 has two open positions as are illustrated in FIGS. 7 and 9. FIG. 7 illustrates what may be referred to as the fully opened position and FIG. 9 illustrates what may be referred to as the half-open position. As will be more fully explained hereinafter, one of the major advantages of the present invention is that all of the contents of the emergency medical pack are readily accessible when the pack is in the half-open position as well as when the pack is in the fully opened position.

Pack 10 is opened to the half-open position by pulling slides 32 to midline 120 on each side of the pack and by folding the upper half of front 12 back onto the lower half. In the half-open position, all of the contents of pack 10 can be accessed without increasing the surface area on which pack 10 rests. The pack is positioned in the fully opened position by moving slides 32 to the bottom of front 12 and folding the entire front back.

With continuing reference to FIGS. 7 and 9, the interior pockets of emergency medical pack 10 are best illustrated. Attached to the interior surface 112 of front 12 are seven pockets in the illustrated preferred embodiment. Pocket 114 is located on the lower half of front 12 and extends from side 16 to side 18 and from midline 120 to the bottom of front 12. Pocket 114 is attached to the interior lining of front 12 by suitable means such as by sewing. The opening 116 of pocket 114 is located along midline 120 such that when pack 10 is in the half-open position as illustrated in FIG. 9, the contents of pocket 114 can still be accessed. Flap 118 extends along opening 116 and can be secured by Velcro fasteners or other means to securely close pocket 114.

Located above midline 120 are interior pockets 122, 126, 130, 134, 138 and 142. These pockets are similar in configuration to pocket 114, but are all smaller and vary in size to accommodate different types of equipment. Each of pockets 114, 122, 126, 130, 134, 138, and 142 includes a label 146 on which the name of the contents of the respective pocket can be written. Accordingly, the contents of each pocket can be determined by the size of the pocket as well as by reading the identification label.

Pockets 122, 126, 130, 134, 138 and 142 are all attached to a separate sheet of material which forms their backs. This sheet is securely attached along its top and sides to the interior lining of front 12. Thus, an additional pocket is located beneath pockets 122, 126, 130, 134, 138 and 142 which has an opening 124 along midline 120. Tab 128 is utilized to open opening 124 which is secured by Velcro fasteners.

Figure 10:
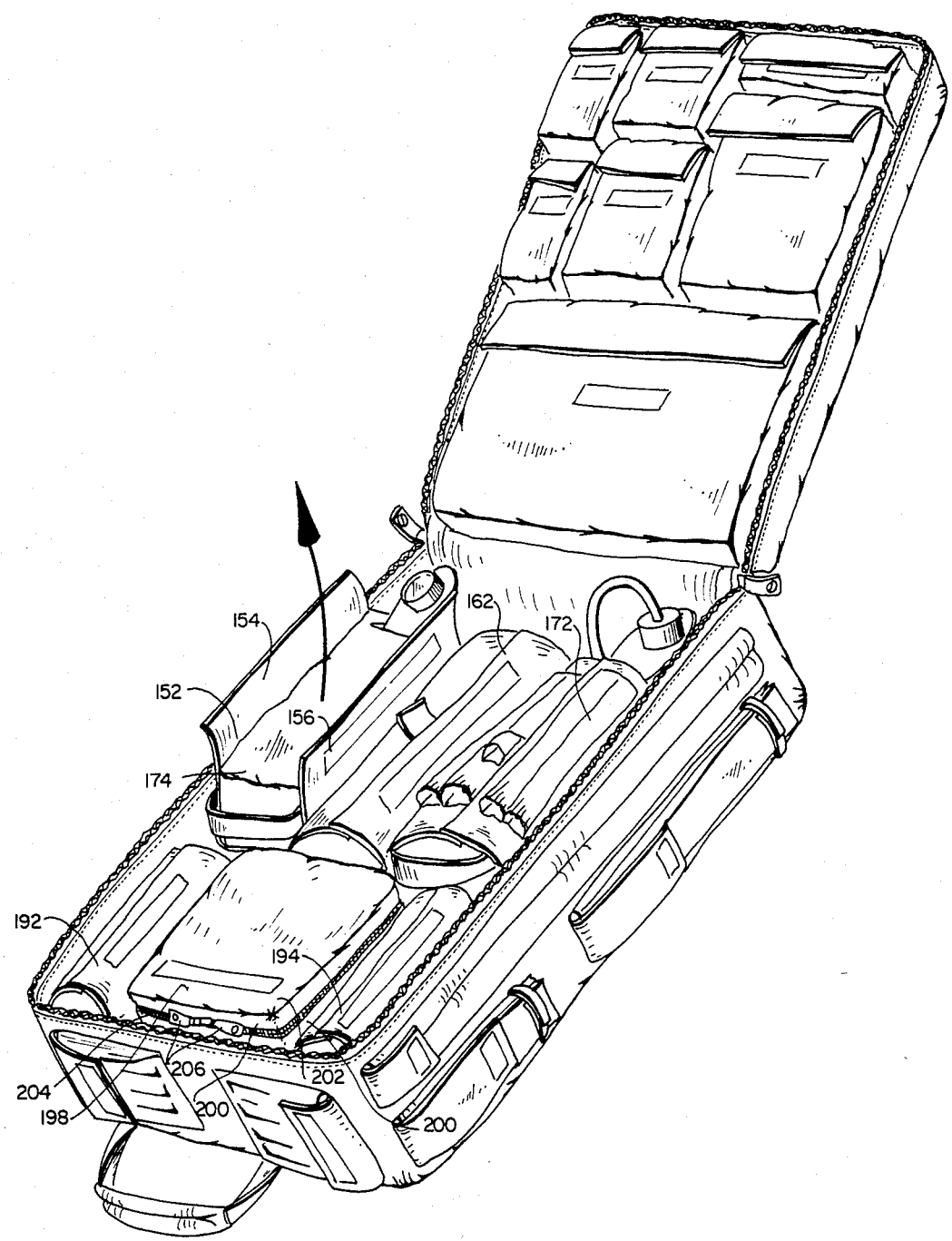
FIG. 10 is a perspective view of the emergency medical pack in the fully opened position illustrating the removal of the contents from one of the open drawer pockets through the top entrance.

Referring now to FIGS. 7 and 10, located within body 150 of pack 10 are six major pockets. The three pockets 152, 162, and 172 which are located in the lower half of body 150 are referred to as open drawer pockets. The unique design of these pockets allows their contents to be accessed when pack 10 is in either the half-open or fully opened position. Each of pockets 152, 162, and 172 comprises a sheet of nylon fabric or other suitable material which is securely attached along its center to bottom 22 of pack 10. Alternatively, pockets 152, 162 and 172 could be formed from two separate sheets of material, each attached alone one side to bottom 22.

Pockets 152, 162, and 172 are illustrated in their closed position in FIG. 7. Open drawer pocket 152 is illustrated in the open position in FIG. 10. Pocket 152 comprises a first side 154 and a second side 156.

The contents of pocket 152 are contained within a pouch 174 which is more fully described hereinafter. The medical equipment contained in pouch 174 is positioned between sides 154 and 156 which are then folded over pouch 174 and are secured as illustrated in FIG. 7 by a Velcro fastener.

The ends 158 and 160 of open drawer pocket 152 are left open. Thus, pouch 174 containing the equipment stored in pocket 152 can be removed either by pulling pouch 174 out of end 158 as illustrated in FIG. 9 if pack 10 is in the half-open or full opened position or by separating sides 154 and 156 of pocket 152 as illustrated in FIG. 10 and lifting pouch 174 out if pack 10 is in the full-open position.

The design of open drawer pockets 152, 162, and 172 allows the contents of these pockets to be easily accessed even when the pack is only in the half-open position. This is significant because space is limited in emergency vehicles, and there often is not sufficient room to open the emergency medical pack to the fully opened position to obtain the necessary equipment to perform required life saving procedures.

In the preferred embodiment, open drawer pockets 152, 162, and 172 contain IV solutions. These are packed in pouches such as pouch 174 (See FIG. 10) to facilitate their removal and to also allow the contents to be easily carried to a second or third patient at the scene of an accident involving multiple injuries or illnesses. Compared to other emergency medical packs, the pack of the present invention does not limit the supplying of medical equipment at the scene of an accident involving many victims to only one victim at a time. The equipment can be dispersed from this pack from a central location for use among many patients at one time rather than requiring the whole medical pack to be carried from one victim to another. Carrying the pack from one patient to another substantially delays the implementation of emergency medical care while central dispersion of medical equipment markedly improves the speed at which specialized medical equipment is delivered to multiple injured patients.

Open drawer pocket 172 is shown in greater detail in the closed position in FIG. 8. Pocket 172 comprises sides 170 and 171 which are sealingly closed with Velcro fasteners and are opened by pulling on tab 172. Slot pockets 166 and 167 are located on flaps 170 and 171 respectively. Slot pockets 166 and 167 are sewn onto flaps 170 and 171 and have elasticized open ends 164. Intravenous catheters or other similar equipment can be stored in these slot pockets. Open drawer pockets 152 and 162 can also include similar slot pockets.

Located on the sides 170 and 171 of pocket 172 are straps 168 and 169. These straps are sewn to sides 170 and 171 along the edges which are parallel to the edge of the side which is connected to pack 10. Accordingly, additional equipment such intubation tubes can be slid underneath straps 168 and 169 and secured in place.

Pouch 174 is illustrated in greater detail in FIGS. 11 and 12. Pouch 174 is generally box-like in configuration having a bottom 176, sides 178 and 180, top end 182, bottom end 184, cover flaps 186 and 188 and a strap 190. The medical equipment is placed within pouch 174 and cover flaps 186 and 188 are folded over the top and secured by Velcro fasteners. Pouch 174 can then be placed between sides 154 and 156 of pocket 152 and secured in place.

Pouch 174 is removed from the open drawer pocket either by grasping strap 190 and pulling the pouch out the open end or by opening flaps 154 and 156, and lifting the pouch out. The contents of pouch 174 can then be removed by opening flaps 186 and 188 by pulling on tab 192. Alternatively, the contents of pouch 174 can be accessed if pack 10 is in the fully opened position by opening sides 154 and 156 and flaps 186 and 188, and by directly removing the contents. A label 146 can also be included on pouch 174 to identify its contents.

Referring again now to FIGS. 7, 9, and 10, also located within body 150 of pack 10 are pockets 192, 194, and 198. Pockets 192 and 194 are similar in construction to open drawer pockets 152, 162, and 172 in that they are formed from two sheets of material which are sewn along one edge to the interior surface of back 22 of pack 10. Pocket 194 is formed from sheets 195 and 196 which are folded over the equipment stored therein and are secured by Velcro fasteners. Pocket 192 is identical to pocket 194, but is located adjacent the other side of pack 10.

Pocket 198 is essentially square shaped and is located between pockets 192 and 194. The base of pocket 198 is formed by a portion of back 22. Four side walls 200 are attached to back 22 to form a box-like configuration. A lid 202 is permanently attached to one of side walls 200. A zipper 204 having two slides 206 is attached to the remaining three side walls 200 and the remaining three edges of lid 202. Zipper 204 is used to sealingly close pocket 198.

As can be readily appreciated from the foregoing description, emergency medical pack 10 has numerous pockets to secure and organize emergency medical equipment which may be needed to perform life saving procedures by rescue personnel.

As is illustrated in FIGS. 13 and 14, pack 10 can be worn on the back of a person 111, thus freeing his hands to provide emergency car. FIG. 13 illustrates pack 10 in the closed position such as during transit. FIG. 14 shows pack 10 in the half-open position such that a second person can access all of the life saving equipment without opening the pack to such an extent that it becomes awkward and burdensome to the person carrying it.

Those skilled in the art and those who are frequently called upon to administer emergency medical care will readily appreciate the unique features of the present invention. The pack of the present invention is designed to hold and protect a significant amount of emergency medical equipment. The pack is further designed such that it can be easily carried by hand or worn as a backpack.

The split-back lid which allows all of the contents of the pack to be accessed when the pack is in the half-open as well as the fully opened position is a significant improvement over prior art packs. The pack can be accessed by a second person while the bearer still has it on his back. More importantly, the contents of the pack can be accessed in confined spaces such as helicopters, airplanes, and ambulances while transporting victims if emergencies arise during transit.

It will of course be appreciated by those skilled in the art that the arrangement and size of the various pockets can be varied to accommodate specific needs. For example, a pack could be designed specially for the treatment of burn victims or it could be designed for coronary care. Also, the specific design might be altered depending upon whether the pack will be used in a helicopter, ambulance, airplane, or hospital emergency room, or whether it will be used in an arctic climate or a jungle.

As will be readily appreciated, the invention may be embodied in other specific forms without departing from the spirit or essential characteristics. The described embodiments are to be considered in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by U.S. Letters Patent is:

1. A medical pack for storing medical equipment, the pack comprising:
    a body having a generally planar back with a plurality of sides extending upwardly from the peripheral edges of said back;
    lid means forming a front on said back, said lid means being attached along a portion of one end thereof to at least one of said sides of said body, and said lid means being configured so as to provide a plurality of operable positions, each permitting user access to substantially all materials contained within the pack;
    a connecting means for detachably securing said lid means along its remaining edges to said sides of said pack; and
    at least one drawer pocket means located in the pack, each of said drawer pocket means securing a pouch within the pack, each said drawer pocket means being formed as a receptacle for said pouch with at least one side of each said drawer pocket means being capable of being opened such that said pouch is removable from the drawer pocket means, said pouch having a handle mounted to one end thereof for use in removing said pouch from said drawer pocket means, said pouch providing storage for medical equipment such that the medical equipment stored in the pouch is accessible by opening the drawer pocket neans when the pouch remains within the pack or by pulling on the handle to slide the pouch from the drawer pocket means of the pack.

2. A medical pack as defined in claim 1 wherein said pack comprises at least two drawer pockets.

3. A medical pack as defined in claim 2 wherein said pouches within said drawer pockets contain medical equipment for performing individual medical procedures and wherein said pouches can be readily removed from the drawer pockets without releasing the pocket means which secures the pouches.

4. A medical pack as defined in claim 1 wherein said connecting means comprises a zipper.

5. A medical pack as defined in claim 1 further comprising means for transporting said pack.

6. A medical pack as defined in claim 5 wherein said transporting means comprises handles whereby said pack can be carried by hand.

7. A medical pack as defined in claim 5 wherein said transporting means comprises shoulder straps such that said pack can be worn by a carrier on his back.

8. A medical pack as defined in claim 1 further comprising pockets attached to at least one exterior surface of said pack.

9. An emergency medical pack for storing and transporting medical equipment to treat a seriously ill or injured person, the medical pack comprising:
    a body having a generally planar back with at least three sides extending upwardly from the peripheral edges of said back;
    lid means forming a front on said pack, said lid means being attached along a portion of one end thereof to one of said sides of said body, said lid means being configured so as to have operable positions of at least a closed position and a partially open position, said lid means being foldable at at least one position along its width so as to place it in said partially open position, the pack occupying substantially the same amount of surface space when the lid is in the partially open position as when the lid is in the closed position and user access to substantially all materials within the pack being permitted when the lid is in the partially open position;
    a connecting means for detachably securing said lid means along its remaining edges to said sides of said pack; and
    a plurality of pockets for securing and organizing medical equipment stored in said pack, at least one of said pockets being attached to said lid means and at least one of said pockets being attached to said body, at least one of said pockets attached to said body having an opening substantially adjacent to said foldable position of said lid means so as to permit user access into that pocket when said lid means is in the partially open position, all of said pockets being oriented in the same direction within said pack when said pack is completely closed such that the contents of all of said pockets are accessible when said pack is in either the fully open or the partially open position.

10. An emergency medical pack as defined in claim 9 wherein at least one of said pockets comprises a drawer pocket.

11. An emergency medical pack as defined in claim 10 wherein said pack further comprises a removable pouch located within said drawer pocket and wherein said pouches contain medical equipment for performing individual medical procedures and wherein said pouches are transportable to a remote location.

12. A medical pack as defined in claim 9 wherein said connecting means comprises a zipper.

13. A medical pack as defined in claim 9 further comprising means for transporting said pack.

14. A medical pack as defined in claim 13 wherein said transporting means comprises handles whereby said pack can be carried by hand.

15. A medical pack as defined in claim 13 wherein said transporting means comprises shoulder straps such that said pack can be worn by a carrier on his back.

16. A medical pack as defined in claim 9 further comprising a plurality of slotted pockets attached to at least one exterior surface of said pack.

17. A medical pack for storing and transporting emergency medical equipment comprising:
   a body;
   a split-back lid being configured so as to have operable positions of at least a closed position, a partially open position, and a fully open position, said lid being foldable at at least one position along its width so as to place it in said partially open position, the pack occupying substantially the same amount of surface space when the lid is in the partially open position as when the lid is in the closed position and user access to substantially all materials within the pack being permitted when the lid is in the partially open position;
   at least two drawer pockets located within the interior of said pack for securing and organizing medical equipment stored in said pack, at least one of said drawer pockets being attached to said lid and at least one of said drawer pockets being attached to said body, at least one of said drawer pockets attached to said body having an opening substantially adjacent to said foldable position of said lid so as to permit user access into that drawer pocket when said lid is in the partially open position all of said drawer pockets being oriented in the same direction within said pack when said pack is completely closed such that the contents of all of said drawer pockets are accessible when said pack is in either the fully open or the partially open position, each said drawer pocket comprising:
   a first side generally rectangular in shape and being securely attached along one edge thereof to said body;
   a second side generally rectangular in shape and being securely attached along one edge thereof to said body in a position substantially parallel to said first side;
   fastening means along a distal edge of both said first and second parallel sides, said fastening means being designed so as to secure said distal edge of said first side to said distal edge of said second side.

18. A medical pack for storing and transporting emergency medical equipment as defined in claim 17 wherein said first and said second sides of each said drawer pocket are formed from a single sheet of material which is fastened along a center portion thereof to said pack.

19. A medical pack for storing and transporting emergency medical equipment as defined in claim 17 wherein said first and said second sides of each said drawer pocket are formed from separate sheets of material.

20. A medical pack for storing and transporting emergency medical equipment as defined in claim 17 further comprising a pouch means for holding medical equipment, said pouch means being positioned within at least one of said drawer pockets.

21. A medical pack for storing and transporting emergency medical equipment as defined in claim 17 further comprising labels on an exterior surface of each drawer pocket for identifying the contents of said pocket.

22. A medical pack for storing and transporting emergency medical equipment as defined in claim 17 further comprising means for transporting said pack.

23. A medical pack as defined in claim 22 wherein said transporting means comprises handles whereby said pack can be carried by hand.

24. A medical pack as defined in claim 22 wherein said transporting means comprises shoulder straps such that said pack can be worn by a carrier on his back.

25. An emergency medical pack for storing, transporting, and protecting medical equipment for treating a seriously ill or injured person, the medical pack comprising:
   a body having a generally planar back with at least three sides extending upwardly from the peripheral edges of said back;
   a lid forming a front on said pack, said lid being attached along a portion of one end thereof to said bottom of said body, said lid having a flexible portion and being configured so as to have operable positions of at least a closed position, a partially open position, and a fully opened position, said lid being foldable at at least one position along its width so as to place it in said partially open position, the pack occupying substantially the same amount of surface space when the lid is in the partially open position as when the lid is in the closed position and user access to substantially all materials within the pack being permitted when the lid is in the partially open position;
   a connecting means for detachably securing said lid along its remaining edges to said sides of said pack;
   a plurality of exterior pockets located on the lid and sides of said pack;
   a plurality of drawer pockets located in the interior of said pack for securing and organizing medical equipment stored in said pack, at least one of said drawer pockets being attached to said lid and at least one of said drawer pockets being attached to said body, at least one of said drawer pockets attached to said body having an opening substantially adjacent to said foldable position of said lid so as to permit user access into that drawer pocket when said lid is in the partially open position, all of said drawer pockets being oriented in the same direction within said pack when said pack is completely closed such that the contents of all of said drawer pockets are accessible when said pack is in either the fully open or the partially open position, each said drawer pocket comprising:
   a first side generally rectangular in shape and being securely attached along one edge thereof to said body of said pack;
   a second side generally rectangular in shape and being securely attached along one edge thereof to said body in a position substantially parallel to said first side;
   fastening means along a distal edge of both said first and said second parallel sides, said fastening means being designed so as to secure said distal edge of said first side to said distal edge of said second side; and a pouch located within each drawer pocket, each said drawer pocket being formed as a receptacle for a corresponding pouch with at least one side of each said drawer pocket being capable of being opened such that said pouch is removable from the drawer pocket, said pouch having a handle mounted to one end thereof for use in removing said pouch from said drawer pocket, said pouch providing storage for medical equipment such that the medical equipment stored in the pouch is accessible by opening the open drawer pocket when the pouch remains within the drawer pocket or by pulling on the handle to slide the pouch from the drawer pocket;

a plurality of additional pockets located in the interior of said pack; and transporting means comprising handles whereby said pack can be carried by hand and shoulder straps such that said pack can be worn as a backpack.

* * * * *

UNITED STATES PATENT AND TRADEMARK OFFICE
CERTIFICATE OF CORRECTION

PATENT NO. : 4,513,866
DATED : April 30, 1985
INVENTOR(S) : Frank O. Thomas

It is certified that error appears in the above-identified patent and that said Letters Patent is hereby corrected as shown below:

```
Column 4, line 44, "is" should be --as--
Column 6, line 30, "persons" should be --person's--
Column 8, line 6, "tab 172" should be --tab 173--
Column 8, line 17, "such" should be --such as--
Column 10, line 2, "neans" should be --means--
Column 11, line 40, "position" should be --position,--
```

Signed and Sealed this

Twenty-fourth Day of September 1985

[SEAL]

Attest:

Attesting Officer

DONALD J. QUIGG

*Commissioner of Patents and Trademarks—Designate*